(12) United States Patent
Dawson et al.

(10) Patent No.: US 9,006,392 B2
(45) Date of Patent: Apr. 14, 2015

(54) ACTAGARDINE DERIVATIVES, AND PHARMACEUTICAL USE THEREOF

(75) Inventors: Michael John Dawson, Welwyn Garden City (GB); Antony Nicholas Appleyard, Welwyn Garden City (GB); Jesus Cortes Bargallo, Welwyn Garden City (GB); Sjoerd Nicolaas Wadman, Welwyn Garden City (GB)

(73) Assignee: Novacta Biosystems Limited, Hertfordshire (GB)

( * ) Notice: Subject to any disclaimer, the term of this patent is extended or adjusted under 35 U.S.C. 154(b) by 0 days.

(21) Appl. No.: 13/576,882

(22) PCT Filed: Feb. 1, 2011

(86) PCT No.: PCT/GB2011/000134
§ 371 (c)(1),
(2), (4) Date: Aug. 2, 2012

(87) PCT Pub. No.: WO2011/095769
PCT Pub. Date: Aug. 11, 2011

(65) Prior Publication Data
US 2012/0302728 A1    Nov. 29, 2012

(30) Foreign Application Priority Data
Feb. 2, 2010   (GB) .................................. 1001688.9

(51) Int. Cl.
| | | |
|---|---|---|
| *A61K 38/00* | (2006.01) | |
| *A61K 38/12* | (2006.01) | |
| *A61K 38/10* | (2006.01) | |
| *C07K 7/08* | (2006.01) | |
| *C07K 16/18* | (2006.01) | |
| *A61K 39/395* | (2006.01) | |

(52) U.S. Cl.
CPC . *C07K 7/08* (2013.01); *A61K 38/10* (2013.01); *A61K 38/00* (2013.01); *C07K 16/18* (2013.01); *A61K 38/12* (2013.01); *A61K 39/39533* (2013.01)

(58) Field of Classification Search
CPC ....... A61K 38/00; A61K 38/12; A61K 38/10; A61K 39/39533; C07K 6/18; C07K 7/08; C07K 16/18
USPC ................... 514/2.9, 2.4, 2.7, 21.1, 2.3, 21.4; 530/317, 300, 326
See application file for complete search history.

(56) References Cited

U.S. PATENT DOCUMENTS

| | | |
|---|---|---|
| 3,710,795 A | 1/1973 | Higuchi et al. |
| 5,112,806 A | 5/1992 | Chatterjee et al. |
| 5,304,540 A | 4/1994 | Blackburn et al. |
| 5,667,991 A | 9/1997 | Koller et al. |
| 5,683,675 A | 11/1997 | Vedia et al. |
| 5,763,395 A | 6/1998 | Blackburn et al. |
| 5,958,873 A | 9/1999 | Sakr et al. |
| 5,985,823 A | 11/1999 | Goldstein |
| 6,022,851 A | 2/2000 | Vertesy et al. |
| 6,569,830 B1 | 5/2003 | Climo et al. |
| 7,056,942 B2 | 6/2006 | Hildesheim et al. |
| 7,122,514 B2 | 10/2006 | Climo et al. |
| 7,989,416 B2 | 8/2011 | Boakes et al. |
| 8,283,371 B2 | 10/2012 | Wadman |
| 8,329,644 B2 * | 12/2012 | Wadman ........................ 514/2.2 |
| 2004/0101963 A1 | 5/2004 | Bibb et al. |
| 2005/0271650 A1 | 12/2005 | Freimark et al. |
| 2009/0203583 A1 | 8/2009 | Wadman et al. |
| 2010/0048459 A1 | 2/2010 | Boakes et al. |
| 2010/0168410 A1 | 7/2010 | Cade et al. |
| 2010/0179207 A1 | 7/2010 | Wadman |
| 2010/0261638 A1 | 10/2010 | Wadman |
| 2011/0294723 A1 | 12/2011 | Wadman |
| 2011/0306091 A1 | 12/2011 | Boakes et al. |

FOREIGN PATENT DOCUMENTS

| | | |
|---|---|---|
| DE | 19745583 | 4/1999 |
| EP | 0195359 | 9/1986 |
| EP | 0572942 | 12/1993 |
| EP | 0700998 | 3/1996 |
| EP | 1646646 | 3/2007 |
| WO | WO 91/07949 | 6/1991 |
| WO | WO 91/11172 | 8/1991 |
| WO | WO 94/02518 | 2/1994 |
| WO | WO 97/00694 | 1/1997 |
| WO | WO 98/55148 | 12/1998 |
| WO | WO 02/00196 | 1/2002 |
| WO | WO 02/088367 | 11/2002 |
| WO | WO 02/103010 | 12/2002 |

(Continued)

OTHER PUBLICATIONS

"Designing Custom Peptides," from SIGMA Genosys, pp. 1-2, Accessed Dec. 16, 2004.
"Treatment of *Clostridium difficile*-Associated Disease (CDAD)," Obstetrics and Gynecology, 109(4):993-995 (2007).
Altena et al., "Biosynthesis of the lantibiotic mersacidin: organization of a type B lantibiotic gene cluster," Applied and Environmental Microbiology, 66(6):2565-2571 (2000).
Appleyard et al., "NVB302 : Gastrointestinal Stability and in vivo Activity in the Hamster Cecitis Model for *Clostridium difficile* Infection," Poster F1-1520, 49th ICAAC, Sep. 12-15, 2009, San Francisco, USA.
Appleyard et al., "NVB302: A Narrow Spectrum Antibiotic under Development for the Treatment of *Clostridium difficile* Infection," Poster F1-1517, 49th ICAAC, Sep. 12-15, 2009, San Francisco, USA.

(Continued)

*Primary Examiner* — Julie Ha
(74) *Attorney, Agent, or Firm* — Morgan, Lewis & Bockius LLP

(57) ABSTRACT

Described are lantibiotic-based compounds, pharmaceutical compositions comprising the same and use of the compounds and said compositions, for the treatment of microbial infection, for example *Clostridium difficile* or *Micrococcus luteus* infection. The lantibiotic-based compounds have antimicrobial activity and in comparison to one or more of actagardine, actagardine B, deoxyactagardine B and deoxyactagardine have retained activity or improved activity.

23 Claims, No Drawings

(56) References Cited

FOREIGN PATENT DOCUMENTS

| WO | WO 03/099862 | 12/2003 |
|---|---|---|
| WO | WO 2004/033706 | 4/2004 |
| WO | WO 2005/093069 | 10/2005 |
| WO | WO 2006/080920 | 8/2006 |
| WO | WO 2007/036706 | 4/2007 |
| WO | WO 2007/083112 | 7/2007 |
| WO | WO 2008/151434 | 12/2008 |
| WO | WO 2009/010763 | 1/2009 |
| WO | WO 2009/010765 | 1/2009 |
| WO | WO 2010/058238 | 5/2010 |
| WO | WO 2010/082018 | 7/2010 |
| WO | WO 2010/082019 | 7/2010 |
| WO | WO 2010/089544 | 8/2010 |
| WO | WO 2011/095768 | 8/2011 |

OTHER PUBLICATIONS

Arioli et al., "Gardimycin, a new anitbiotic from *Actinoplanes*: III. Biological properties" The Journal of Antibiotics, 29(5):511-515 (1976).
Berendsen, "A Glimpse of the Holy Grail?," Science, 282: 642-643 (1998).
Berge et al., "Pharmaceutical salts," Journal of Pharmaceutical Sciences, 66(1):1-19 (1977).
Bierbaum et al., "Cloning, sequencing and production of the lantibiotic mersacidin," FEMS Microbiology Letters, 127:121-126 (1995).
Bierman et al., "Plasmid cloning vectors for the conjugal transfer of DNA from *Escherichia coli* to *Streptomyces* spp.," Gene, 116(1): 43-49 (1992).
Boakes et al., "Organization of the biosynthetic genes encoding deoxyactagardine B (DAB), a new lantibiotic produced by *Actinoplanes liguariae* NCIMB41362," The Journal of Antibiotics, 63:351-358 (2010).
Boakes et al., "Organization of the genes encoding the biosynthesis of actagardine and engineering of a variant generation system," Molecular Microbiology, 72(5):1126-1136 (2009).
Bradley et al. "Limits of cooperativity in a structurally modular protein: Response of the notch ankyrin domain to analogous alanine substitutions in each repeat," J. Mol. Biol., 324: 373-386 (2002).
Britton et al., "Genome-Wide Analysis of the Stationary-Phase Sigma Factor (Sigma-H) Regulon of *Bacillus subtilis*," Journal of Bacteriology, 184(17):4881-4890 (2002).
Castiglione et al., "A novel lantibiotic acting on bacterial cell wall synthesis produced by uncommon actinomycete *Planomonospora* sp.," Biochemistry, 46:5884-5895 (2007).
Chatterjee et al., "Biosynthesis and Mode of Action of Lantibiotics," Chem. Rev. 105:633-683 (2005).
Clostridial intra-abdominal infections from Merck Manual, http://merckmanual.com/professional/sec15/ch189/ch189f.html, pp. 1-2, Accessed Aug. 10, 2011.
*Clostridium difficile*-induced diarrhea from Merck Manual, http://merckmanual.com/professional/sec15/ch189e.html, pp. 1-2, Accessed Aug. 10, 2011.
Coronelli et al., "Gardimycin, A New Antibiotic From *Actinoplanes*: II. Isolation and preliminary characterization," Journal of Antibiotics, 29(5):507-510 (1976).
Cotter et al., "Bacterial lantibiotics: strategies to improve therapeutic potential," Current Protein Peptide Science, 6(1):61-75 (2005).
Dabard et al., "Ruminococcin A, a new lantibiotic produced by a *Ruminococcus gnavus* strain isolated from human feces," Appl. Environ. Microbiol., 67:4111-4118 (2001).
Dawson, "Lantibiotics as antimicrobial agents," Expert Opinion on Therapeutic Patents, Informa Healthcare, GB, 17(4):365-369 (2007).
de Vos et al., "Maturation pathway of nisin and other lantibiotics: post-translationally modified antimicrobial peptides exported by gram-positive bacteria," Molecular Micobiology, 17(3):427-437 (1995).
Definition of moiety, from http://dictionary.reference.com/browse/moiety, pp. 1-3, Accessed Aug. 26, 2010.
Dower et al., "High efficiency transformation of *E. coli* by high voltage electroporation," Nucleic Acids Research, 16(13):6127-6145 (1988).
European Search Report issued in European Patent Application No. EP 10 00 0424 dated Apr. 21, 2010.
Examination Report for New Zealand Patent Application No. 569486 dated Apr. 27, 2010.
Examination Report for New Zealand Patent Application No. 569486 dated Mar. 10, 2011.
Fleisher et al., "Improved oral drug delivery: solubility limitations overcome by the use of prodrugs," Advanced Drug Delivery Reviews, 19(2):115-130 (1996).
Flett et al., "High efficiency intergeneric conjugal transfer of plasmid DNA from *Escherichia coli* to methyl DNA-restricting Streptomycetes," FEMS Microbiology Letters, 155(2): 223-229 (1997).
Fukase et al., "Synthetic study of peptide antibiotic nisin. V. Total synthesis of nisin," Bull. Chem. Soc. Jpn., 65:2227-2240 (1992).
Fumi et al., "Rifaximin treatment for symptoms of irritable bowel syndrome," The Annals of Pharmacotherapy, 42:408-412 (2008).
Gardiner et al., "Fate of the Two-Component Lantibiotic Lacticin 3147 in the Gastrointestinal Tract," Applied and Environmental Microbiology, 73(21):7103-7109 (2007).
Gravesen et al., "pbp2229-Mediated nisin resistance mechanism in *Listeria monocytogenes* confers cross-protection to class IIa bacteriocins and affects virulence gene expression," Applied and Environmental Microbiology, 70(3): 1669-1679 (2004).
Guder et al., "Role of the single regulator MrsR1 and the two-component system MrsR2/K2 in the regulation of mersacidin production and immunity," Applied and Environmental Microbiology, 68(1):106-113 (2002).
Guiotto et al., "PEGylation of the antimicrobial peptide nisin A: problems and perspectives," Il Farmaco, 58(1):45-50 (2003).
Gust et al., "PCR-targeted *Streptomyces* gene replacement identifies a protein domain needed for biosynthesis of the sesquiterpene soil odor geosmin," PNAS, 100(4): 1541-1546 (2003).
Gust et al., "λ Red-mediated genetic manipulation of antibiotic-producing *Streptomyces*," Advances in Applied Microbiology , 54:107-128 (2004).
Han, "Advances in characterization of pharmaceutical hydrates," Trends in Bio/Pharmaceutical Industry, 25-29 (Mar. 2006).
Heinzelmann et al., "A glutamate mutase is involved in the biosynthesis of the lipopeptide antibiotic friulimicin in *Actinoplanes friuliensis*," Antimicrobial Agents and Chemotherapy, 47(2): 447-457 (2003).
Hilger et al., "Differential binding of IgG and IgA antibodies to antigenic determinants of bovine serum albumin," Clin. Exp. Immunol., 123:387-394 (2001).
Holtsmark et al., "Purification, Characterization, and Gene Sequence of Michiganin A, an Actagardine-Like Lantibiotic Produced by the Tomato Pathogen *Clavibacter michiganensis* subsp. *michiganensis*," Applied and Environmental Microbiology, 72(9):5814-5821 (2006).
International Preliminary Report on Patentability in PCT/GB2010/000043 dated Apr. 14, 2011.
International Preliminary Report on Patentability in PCT/GB2010/000042 dated Apr. 19, 2011.
International Preliminary Report on Patentability in PCT/GB2010/000188 dated Apr. 19, 2011.
International Search Report and Written Opinion for PCT/GB2010/000042 dated May 20, 2010.
International Search Report and Written Opinion for PCT/GB2010/000188 dated May 20, 2010.
International Search Report and Written Opinion for PCT/GB2010/000043 dated Mar. 29, 2010.
Jack et al., "The genetics of lantibiotic biosynthesis," Bioessays, 17(9):793-802 (1995).
Kettenring et al., "Sequence determination of actagardine, a novel lantibiotic, by homonuclear 2D NMR spectroscopy," J. Antibiot., 43(9):1082-1088 (1990).
Lonetto et al., "The sigma 70 family: sequence conservation and evolutionary relationships," Journal of Bacteriology, 174(12): 3843-3849 (1992).

(56) References Cited

OTHER PUBLICATIONS

Louie et al., "A phase 2 study of the toxin binding polymer tolevamer in patients with *C. difficile* associated diarrhoea," Proceedings of 14th European Congress of Clinical Microbiology and Infectious Diseases, Prague Congress Centre, Prague, Czech Republic, p. 548 (May 1-4, 2004).
Louie et al., "Tolemaver (GT160-246) binds *Clostridium* cytotoxins A/B and is associated with restoration of components of the anaerobic intestinal microflora during treatment of *C. difficile* associated diarrhoea," Proceedings of 14th European Congress of Clinical Microbiology and Infectious Diseases, Prague Congress Centre, Prague, Czech Republic, p. 855 (May 1-4, 2004).
Malabarba et al., "Physico-chemical and biological properties of actagardine and some acid hydrolysis products," The Journal of Antibiotics, 38(11):1506-1511 (1985).
Malabarba et al., "Synthesis and biological activity of some amide derivatives of the lantibiotic actagardine," The Journal of Antibiotics, 43(9):1089-1097 (1990).
Marahiel et al., "Regulation of peptide antibiotic production in *Bacillus*," Molecular Microbiology, 7(5):631-636 (1993).
McClerren et al., "Discovery and in vitro biosynthesis of haloduracin, a two-component lantibiotic" PNAS, 103(46):17243-17248 (2006).
Miner et al., "Steroid-refractory ulcerative colitis treated with corticosteroids, metronidazole and vancomycin: a case report," BMC Gastroenterology 5:3 (2005).
Ngo et al. "Computational Complexity, Protein Structure Prediction, and the Levinthal Paradox," The Protein Folding Problem and Tertiary Structure Prediction, K. Merc JT. and S. Le Grand Edition, 491-495 (1994).
Non-final office action issued in U.S. Appl. No. 12/686,135 dated Apr. 28, 2011.
Notice of Allowance mailed in U.S. Appl. No. 12/161,221 dated May 12, 2011.
Office Action issued in Chinese Application No. 200780006748.0 dated Mar. 23, 2011 (Translation included).
Office Action issued in European Patent Application No. 07704921.1 dated Aug. 30, 2010.
Office Action issued in European Patent Application No. 07704921.1 dated Apr. 7, 2010.
Office Action issued in European Patent Application No. 10000424.1 dated May 19, 2011.
Office Action issued in European Patent Application No. 10700336.0 dated May 3, 2012.
Office Action issued in European Patent Application No. 10702536.3 dated May 11, 2012.
O'Sullivan et al., "High- and low-copy-number *Lactococcus* shuttle cloning vectors with features for clone screening," Gene, 137:227-231 (1993).
Parenti et al., "Gardimycin, a new antibiotic from *Actinoplanes*. I. Description of the producer strain and fermentation studies," The Journal of Antibiotics, 29(5):501-506 (1976).
Rea et al., "Antimicrobial activity of lacticin 3147 against clinical *Clostridium difficile* strains," Journal of Medical Microbiology, 56:940-946 (2007).
Rey et al., "Complete genome sequence of the industrial bacterium *Bacillus licheniformis* and comparisons with closely related *Bacillus* species," Genome Biology, 5(10):R77 (2004).
Rudinger J, "Characteristics of the amino acids as components of a peptide hormone sequence," Peptide Hormones, JA Parsons Edition, University Park Press, Jun. 1976, pp. 1-7.
Sahl et al., "Lantibiotics: Biosynthesis and biological activities of uniquely modified peptides from gram-positive bacteria," Ann. Rev. Microbiology, 52:41-79 (1998).
Schinzel et al. "The phosphate recognition site of *Escherichia coli* maltodextrin phosphorylase," FEBS, 286(1,2): 125-128 (1991).
Somma et al., "Gardimycin, a new antibiotic inhibiting peptidoglycan synthesis," Antimicrobial Agents and Chemotherapy, 11(3):396-401 (1977).
Szekat et al., "Construction of an expression system for site-directed mutagenesis of the lantibiotic mersacidin," Applied and Environmental Microbiology, 69(7):3777-3783 (2003).
Translation of Israeli Examination Report for Israeli Patent Application No. 192446 dated Apr. 22, 2010.
Turner et al., "Solution structure of plantaricin C, a novel lantibiotic," Eur. J. Biochem., 264:833-839 (1999).
Turtell et al., "The use of nisin in cheesemaking. Chapter 5: International acceptance of nisin as a food preservative," Bulletin of the Int. Dairy Fed., 329:20-23 (1988).
Ugurlu et al., "Colonic delivery of compression coated nisin tablets using pectin/HPMC polymer mixture," Eur. J. Pharm. Biopharm., 67:202-210 (2007).
van Kraaij et al., "Lantibiotics: biosynthesis, mode of action and applications," Nat. Prod. Rep., 16:575-587 (1999).
Vertesy et al., "Ala(0)-actagardine, a new lantibiotic from cultures of *Actinoplanes liguriae* ATCC 31048," Journal of Antibiotics, Japan Antibiotics Research Association, 52(8):730-741 (1999).
Vippagunta et al., "Crystalline solids," Advanced Drug Delivery Reviews, 48(1):3-26 (2001).
Voet et al., "Abnormal Hemoglobins," Biochemistry, Second Edition, John Wiley & Sons, Inc., pp. 235-241 (1995).
Wadman et al., "NVB302: In vitro Activity Against *Clostridium difficile* and Intestinal Strains of Anaerobic Bacteria," Poster F1-1518, 49th ICAAC, Sep. 12-15, 2009, San Francisco, USA.
Widdick et al., "Cloning and engineering of the cinnamycin biosynthetic gene cluster from *Streptomyces cinnamoneus cinnamoneus* DSM 40005," PNAS, 100(7):4316-4321 (2003).
Wikipedia, the free encyclopedia, "Lanthionine," http://en.wikipedia.org/wiki/Lanthionine, (Nov. 2, 2011).
Written Opinion of the International Preliminary Examining Authority in PCT/GB2010/000043, dated Feb. 1, 2011.
Zimmerman et al., "The tetracyclic lantibiotic actagardine H-NMR and C-NMR assignments and revised primary structure," European Journal of Biochemistry, 228(3):786-797 (1995).
Zimmermann et al., "The three-dimensional solution structure of the lantibiotic murein-biosynthesis-inhibitor actagardine determined by NMR," Eur. J. Biochem., 246:809-819 (1997).

\* cited by examiner

ACTAGARDINE DERIVATIVES, AND PHARMACEUTICAL USE THEREOF

RELATED APPLICATIONS

The present application is a U.S. National Phase Application of International Application No. PCT/GB2011/000134 filed 1 Feb. 2011, which claims priority to GB Patent Application No. GB1001688.9 filed 2 Feb. 2010, each of which is incorporated herein by reference in its entirety.

This application is related to GB patent application GB1001688.9 filed 2 Feb. 2010; the contents of which are incorporated herein by reference in their entirety.

The present disclosure relates to certain novel compounds, pharmaceutical compositions comprising the same and use of the compounds and said compositions, for the treatment of microbial infection, for example *Clostridium difficile* or *Micrococcus luteus* infection.

Many antibiotic compounds have been identified from natural sources including microorganisms. Often the antibiotic compounds have a complicated chemical structure and in particular a complicated stereochemical structure.

Actagardine is a natural product prepared from *Actinoplanes garbadinensis*, and has antibiotic properties, see for example EP0195359, in particular against *Streptococcus pyogenes*, which causes scarlet fever and strep throat infection. Despite the need for new antibiotics in the 22 years since publication of EP0195359, no antibiotics derived from actagardine have been licensed and marketed.

A new family of compounds based on deoxyactagardine B was recently disclosed in WO 2007/083112. Deoxyactagardine B is prepared from *Actinoplanes. liguriae* and has a number of distinguishing features from actagardine. The document disclosed for the first time the sequence of the genes that synthesise actagardine and deoxyactagardine B thereby allowing genetic manipulation of the host to provide variants of the core structure of actagardine and also deoxyactagardine B.

Variations of compounds is important because: Firstly, it allows the properties of the individual molecules to be optimised in a number of different respects including activity against particular organisms, stability, expressibility, and other physical properties that, for example can be important in formulation of the active ingredient. Secondly, a diverse range of antibiotics are required to cope with the developed resistance of microbes to existing treatments.

The present inventors have now established that modifications at a number of positions in the core structure are not well tolerated in that they lead to a loss in activity. These modifications are undesirable. However, a number of single point mutations are tolerated in the core structure such that desirable antimicrobial activity is retained or increased.

The present disclosure provides a compound of formula (I):

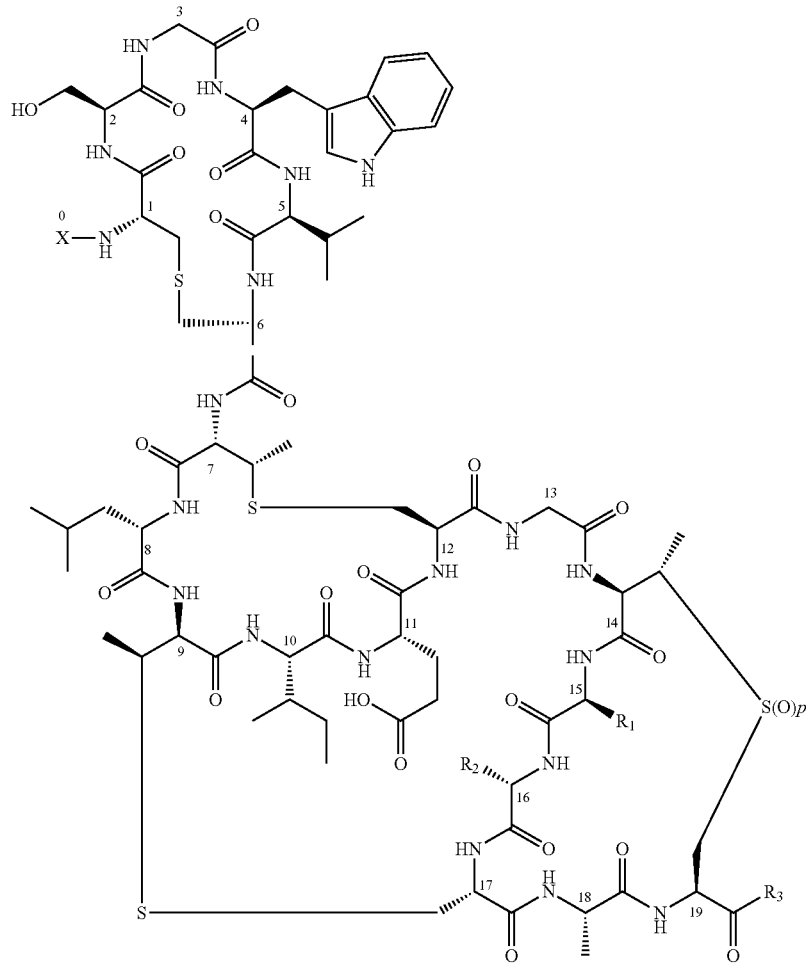

(I)

wherein:

X represents H or an amino acid;

p is 0 or 1;

$R_1$ represents —CH(CH$_3$)$_2$ or —CH$_2$CH(CH$_3$)$_2$;

$R_2$ represents —CH(CH$_3$)CH$_2$CH$_3$ or —CH(CH$_3$)$_2$;

$R_3$ represents —OH or —ZNR$^4$R$^5$;

Z is a bond or an amino acid;

$R^4$ represents hydrogen, or $C_{1-10}$ branched or unbranched alkyl wherein one, two or three carbons are optionally replaced by a heteroatom and said alkyl chain optionally bears 1 or 2 oxo substituents, and/or optionally bears a 5 to 6 membered heterocyclyl, $R^5$ represents hydrogen, —R$^A$-L-Ar$^1$ or $C_{1-10}$ branched or unbranched alkyl wherein one, two or three carbons are optionally replaced by a heteroatom and said alkyl chain is optionally bears 1 or 2 oxo substituents and/or optionally bears one 5 to 6 membered heterocyclyl, or $R^4$ together with $R^5$ and the nitrogen to which they are attached form a 5 or 6 membered heterocyclic group optionally including a further heteroatom selected from N, O or S, wherein said heterocyclic group is optionally substituted by:

$C_{0-10}$ branched or unbranched alkyl wherein one, two or three carbons are optionally replaced by a heteroatom and said alkyl chain optionally bears 1 or 2 oxo substituents, said alkyl chain optionally substituted by:
$C_{3-7}$ cycloalkyl;
5 to 6 membered heteroaryl;
5 to 6 membered heterocyclyl;
$C_{6-10}$ aryl;
YAr$^1$; or
wherein said heteroaryl, heterocyclyl and aryl are optionally substituted by $C_{1-10}$ branched or unbranched alkyl wherein one, two or three carbons are optionally replaced by a heteroatom and said alkyl chain optionally bears 1 or 2 oxo substituents,
$C_{3-7}$ cycloalkyl;
5 to 6 membered heteroaryl;
5 to 6 membered heterocyclyl;
$C_{3-7}$ aryl
YAr$^1$, or
wherein said heteroaryl, heterocyclyl and aryl are optionally substituted by $C_{1-10}$ branched or unbranched alkyl wherein one, two or three carbons are optionally replaced by a heteroatom and said alkyl chain optionally bears 1 or 2 oxo substituents, $R^A$ represents a bond, —$C_{0-9}$ alkylC$_{6-10}$aryl, —$C_{0-9}$ alkyl$C_{3-11}$ heteroaryl, —$C_{1-9}$ heteroalkylC$_{5-11}$heteroaryl, —$C_{0-9}$ alkylC$_{3-6}$cycloalkyl, or —$C_{0-9}$ alkylC$_{5-11}$ heterocycle;

L represents a straight or branched $C_{0-15}$ alkyl chain wherein optionally one, two or three carbons are replaced by a heteroatom independently selected from N, O or S, wherein said chain is optionally substituted by one or more (e.g. 1 or 2) oxo or nitro groups
with the proviso that a replacement heteroatom is not bonded directly to the N of the group —NR$^3$R$^4$;

Y represents a straight or branched $C_{0-15}$ alkyl chain wherein optionally one, two or three carbons are replaced by a heteroatom independently selected from N, O or S, wherein said chain is optionally substituted by one or more (e.g. 1 or 2) oxo or nitro groups;

Ar$^1$ represents phenyl substituted by one or two NO$_2$ groups or one to five such as 2, 3, or 4 halogen groups, or one or two $C_{1-3}$ haloalkyl groups, or a combination thereof, characterised in that one or more amino acids at position 2, 3, 4, 5, 8, 10, 11, 13, 15, 16 or 18 in the compound of formula (I) has/have been replaced by an alternative amino acid, with the proviso that when the amino acids are unchanged at positions 2, 3, 4, 5, 8, 10, 11, 13 and 18, and X is selected from H, Ala, Lys and Ile, and p is 1 positions 15 and 16 are not Val, Ile respectively, or X is selected from H and Ala, and p is 0 positions 15 and 16 are not Val, Ile respectively, or X is selected from H and Ala, and p is 1 positions 15 and 16 are not Leu, Val; Val, Val or Leu, Ile respectively, or X is selected from H, Ala, Ile, Phe, Val, Lys and Trp and p is 0 positions 15 and 16 are not Leu, Val respectively.

The compounds of the present disclosure have antimicrobial activity and in comparison to one or more of actagardine, actagardine B, deoxyactagardine B and deoxyactagardine have retained activity or improved activity.

DETAILED DESCRIPTION OF THE INVENTION

Alkyl in the context of the present disclosure refers to straight chain or branched chain alkyl, for example methyl, ethyl, n-propyl, isopropyl, n-butyl or t-butyl.

Heterocyclic group as employed herein is a saturated or partially unsaturated ring (i.e. a non-aromatic mono or bicyclic ring) comprising one or more heteroatoms selected from O, N and S, for example a 5 or 6 membered heterocycle group such as pyrroline (in particular 1, 2 or 3-pyrroline), pyrrolidine, tetrahydrofuran, tetrahydrothiophene, pyrazoline (in particular 2 or 3-pyrazoline), 2-imidazoline, pyrazolidine, imidazolidine, 3-dioxolane, thiazolidine, isoxazolidine, pyran (in particular 2H or 4H-pyran), 3,4-dihydro-2H-pyran, piperidine, 1,4-oxazine, 1,4-dioxine, piperazine, morpholine, 1,4-dioxane. It will be understood that in definitions employed herein, such as $C_{5-11}$ heterocycle, that the heteroatom may replace a carbon atom in the ring and therefore $C_{5-11}$ heterocycle and a 5 to 11 membered heterocycle are used interchangeably. Other definitions of heterocycles will be construed similarly. The heterocycle may be linked through carbon or nitrogen.

In one embodiment the 5 or 6 membered heterocyclyl represents morpholinyl, piperidinyl, pyrollidinyl or thiomorphinyl.

Cycloalkyl as employed herein refers to a saturated or partially unsaturated carbocyclic ring, i.e. a non-aromatic carbocyclic ring, for example cyclopropyl, cyclopentyl or cyclohexyl.

Heteroaryl as employed herein refers to an aromatic carbocycle comprising one or more heteroatoms selected from O, N or S including a bicyclic system wherein one or both rings are aromatic, for example a 5-11 membered heteroaryl, such as pyrrole, furan, thiophene, pyrazole, imidazole, oxazole, isoxazole, thiazole, isothiazole, triazole, oxadiazole, furazan, tetrazole, pyridine, pyridazine, pyrimidine, pyrazine, triazine, 1H-pyrrolizine, indolizine, indole, isoindole, benzofuran, isobenzofuran, indoline, isoindoline, benzothiophene, indazole, benzimidazole, purine, quinoline, isoquinoline, chromane, isochromane, chromene, cinnoline, quinazoline, quinoxaline, naphthyridine or phthalazine. It will be understood that in definitions employed herein, such as $C_{5-11}$ heteroaryl, that the heteroatom may replace a carbon atom in the ring and therefore $C_{5-11}$ heteroaryl and a 5 to 11 membered heteroaryl are used interchangeably. Other definitions of heteroaryls will be construed similarly. The heteroaryl may be linked through carbon or a nitrogen, as appropriate, in particular carbon.

Halogen as employed herein refers to fluoro, chloro or bromo, such as fluoro or chloro.

Haloalkyl as employed herein refers to alkyl groups having 1 to 6 halogen atoms, for example 1 to 5 halogens, such as per haloalkyl, in particular perchloroalkyl or perfluoroalkyl, more specifically —CCl$_2$CCl$_3$, —CF$_2$CF$_3$ or —CF$_3$.

Heteroalkyl as employed herein is an alkyl represents a straight or branched alkyl chain wherein optionally one or more carbons (such as 2 or 3) are replaced by a heteroatom independently selected from N, O or S, wherein said chain is optionally substituted by one or more (for example 1 or 2), oxo or nitro groups. In one embodiment the alkyl in heteroalkyl is a straight chain.

Oxo as employed herein refers to =O.

In relation to a saturated or unsaturated, branched or unbranched alkyl chain, wherein a carbon is replaced by a heteroatom selected from O, N or S, it will be clear to persons skilled in the art that the heteroatom may replace a primary, secondary or tertiary carbon, that is —$CH_3$, —$CH_2$—, a —CH— or a branched carbon group, as technically appropriate.

"Has/have been replaced by an alternative amino acid" as employed herein is intended to refer to the fact that at least one amino acid present in a compound of the invention differs from a relevant one shown in the core structure of a compound of formula (I). It is not intended to limit the compound(s) of the invention in any way by the process they were prepared. The replacement amino acid in each position is independently selected from the amino acids available. The amino acid may be a non-natural or a naturally occurring amino acid, in particular a naturally occurring amino acid.

Amino acid as employed herein is a natural or non-naturally occurring amino acid, for example a natural amino acid such as alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

Position 0 is an amino at the N-terminus of the peptide core structure. Position 0 is represented herein as X in compounds of formula (I).

In one embodiment one amino acid is changed. In one embodiment 2, 3, 4, 5, 6, 7, 8, 9, 10, 11 or 12 amino acids are changed.

In one embodiment position 15 and 16 respectively do not represent Val, Leu; Val, Val; Leu, Ile; Val, Ile or Leu, Val.

The modifications to provide compounds according to the present disclosure are not employed to provide known lantibiotics or fragments of known lantibiotics.

In one embodiment $Ar^1$ represents phenyl substituted by one or two $NO_2$ groups or one to five (such as 2, 3, or 4) halogen groups, or a combination thereof.

In one embodiment $R^1$ is —$CH(CH_3)_2$.
In one embodiment $R^1$ is —$CH_2CH(CH_3)_2$.
In one embodiment $R^2$ is —$CH(CH_3)CH_2CH_3$.
In one embodiment $R^2$ is —$CH(CH_3)_2$.
In one embodiment $R^3$ represents —OH.
In one embodiment $R^3$ represents —$ZNR^4R^5$.
In one embodiment Z represents a bond.
In one embodiment Z represents an amino acid, for example selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

In one embodiment $R^4$ is H.
In one embodiment $R^4$ is $C_{1-10}$ branched or unbranched alkyl wherein in one, two or three carbons are optionally replaced by a heteroatom and said alkyl chain optionally bears 1 or 2 oxo substituents, for example —$(CH_2)_nNR^6R^7$ wherein n is an integer 2-12, such as 3, 4, 5, 6, 7, 8, 9, 10 or 11 and $R^6$ and $R^7$ are independently selected from H and $C_{1-3}$ alkyl such as methyl, to provide a terminal group in particular —$NH_2$, $NHCH_3$ and —$N(CH_3)_2$.

In one embodiment $R^5$ is H.
In one embodiment $R^5$ is $C_{1-10}$ branched or unbranched alkyl wherein in one, two or three carbons are optionally replaced by a heteroatom and said alkyl chain is optionally bears 1 or 2 oxo substituents, for example —$(CH_2)_nNR^6R^7$ wherein n is an integer 2-12, such as 3, 4, 5, 6, 7, 8, 9, 10 or 11 and $R^6$ and $R^7$ are independently selected from H and $C_{1-4}$ alkyl such as methyl, to provide a terminal group in particular —$NH_2$, —$NHCH_3$ and —$N(CH_3)_2$.

In one embodiment $R^5$ is a $C_{1-10}$ branched or unbranched alkyl bearing one 5 to 6 membered heterocyclyl, for example the heterocyclyl is a nitrogen containing heterocyclyl optionally contain one further heteroatom selected from N, O and S, such as pyrollidine, pyridine, piperidine and morpholine. The heterocycle may be linked to the alkyl chain through nitrogen.

In one embodiment $R^5$ represents —$R^A$-L-$Ar^1$.

In one embodiment $R^A$ is a bond. When $R^A$ is a bond then it will be understood that L or $Ar^1$, as appropriate, is directly linked to the nitrogen of —$NR^4R^5$.

In one embodiment $R^A$ is $C_{0-9}$ alkyl$C_{6-10}$aryl, such as $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-phenyl or napthyl, in particular phenyl. When $C_0$ is employed then $C_{6-10}$aryl will be linked directly to the nitrogen of —$NR^4R^5$.

In an alternative embodiment $R^A$ is $C_{0-9}$ alkyl$C_{5-11}$heteroaryl, such as $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-heteroaryl, for example selected from pyrrole, furan, thiophene, pyrazole, imidazole, oxazole, isoxazole, thiazole, isothiazole, triazole, oxadiazole, furazan, tetrazole, pyridine, pyridazine, pyrimidine, pyrazine, triazine, 1H-pyrrolizine, indolizine, indole, isoindole, benzofuran, isobenzofuran, indoline, isoindoline, benzothiophene, indazole, benzimidazole, purine, quinoline, isoquinoline, chromane, isochromane, chromene, cinnoline, quinazoline, quinoxaline, naphthyridine or phthalazine.

In one embodiment $R^A$ is $C_{0-9}$ alkyl$C_{3-6}$cycloalkyl, for example $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-$C_{3-6}$cycloalkyl selected from cyclopropyl, cyclopentyl or cyclohexyl. When $C_0$ is employed then $C_{3-6}$cycloalkyl will be linked directly to the nitrogen of —$NR^4R^5$.

In one embodiment $R^A$ is —$C_{0-9}$ alkyl$C_{5-11}$ heterocyclic group for example $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-heterocyclic group for example selected from pyrroline (such as 1, 2 or 3-pyrroline), pyrrolidine, tetrahydrofuran, tetrahydrothiophene, pyrazoline (such as 2 or 3-pyrazoline), 2-imidazoline, pyrazolidine, imidazolidine, 3-dioxolane, thiazolidine, isoxazolidine, pyran (such as 2H or 4H-pyran), 3,4-dihydro-2H-pyran, piperidine, 1,4-oxazine, 1,4-dioxine, piperazine, morpholine and 1,4-dioxane. When $C_0$ is employed then the $C_{5-11}$ heterocycle will be linked directly to the nitrogen of —$NR^4R^5$.

Clearly $R^A$ is a linking group and thus when it comprises a ring such as a cycloalkyl, heterocycle, heteroaryl or aryl then $LAr^1$ may be attached via the ring.

L in one embodiment is $C_0$. When L is $C_0$ the $Ar^1$ may be linked directly to the nitrogen of —$NR^4R^5$. Alternatively when L is $C_0$ then $Ar^1$ may be linked to $R^A$.

In an alternative embodiment L is a straight or branched, such as straight, $C_{1-9}$ alkyl chain wherein optionally one or more, such as one, carbon(s) is/are replaced by a heteroatom selected from O, N and S, such as N, and optionally substituted by, for example one or two oxo. For example L is a straight $C_{1-3}$ alkyl chain (such as $C_1$ alkyl), wherein none of the carbons are replaced by a heteroatom, in particular wherein the chain does not bear any optional substituents.

Alternatively, L is a straight $C_{6-9}$ alkyl chain, wherein one carbon is replaced by a heteroatom, such as N, and the chain optionally bears one oxo substituent, in particular —$CH_2CH_2CH_2NHCH_2$— or —$CH_2CH_2CH_2NHC(O)$—.

In one embodiment L is —$(CH_2)_iNH(CH_2)_j$— or —$(CH_2)_k$NHC(O)— wherein i is an integer 1 to 12, j is 0 or 1 and k is and integer 1 to 14 such as —$CH_2CH_2CH_2NHCH_2$— or —$CH_2CH_2CH_2NHC(O)$—.

In one embodiment a heteroatom in L is separate from the nitrogen of —$NR^4R^5$ by at least two carbon atoms.

In one embodiment R⁴ together with R⁵ and the nitrogen to which they are attached form a 5 or 6 membered heterocyclic group optionally including a further heteroatom selected from N, O or S, wherein said heterocyclic group is optionally substituted by:
  $C_{0-10}$ branched or unbranched alkyl wherein in one two or three carbons are optionally replaced by a heteroatom and said alkyl chain optionally bears 1 or 2 oxo substituents, said alkyl chain optionally substituted by:
    $C_{3-7}$ cycloalkyl;
    5 to 6 membered heteroaryl;
    5 to 6 membered heterocyclyl;
    $C_{6-10}$ aryl; or
    wherein said heteroaryl, heterocyclyl and aryl are optionally substituted by a $C_{1-10}$ branched or unbranched alkyl wherein in one two or three carbons are optionally replaced by a heteroatom and said alkyl chain is optionally bears 1 or 2 oxo substituents, or
  $C_{3-7}$ cycloalkyl;
  5 to 6 membered heteroaryl;
  5 to 6 membered heterocyclyl;
  $C_{6-10}$ aryl; or
wherein said heteroaryl, heterocyclyl and aryl are optionally substituted by a $C_{1-10}$ branched or unbranched alkyl wherein in one two or three carbons are optionally replaced by a heteroatom and said alkyl chain is optionally bears 1 or 2 oxo substituents.

The 5 or 6 membered heterocyclic group formed by —NR⁴R⁵, for example include piperidine and piperazine.

In one embodiment the cycloalkyl, heteroaryl, heterocyclyl or aryl is linked directly to the 5 or 6 membered heterocyclic group formed by —NR⁴R⁵.

In one embodiment there is a linker, for example —CH₂—, —CH₂NHCH₂—, —CH₂CH₂NHCH₂—, between said 5 or 6 membered heterocyclic group formed by —NR⁴R⁵ and a cycloalkyl, heteroaryl, heterocyclyl or aryl.

In one embodiment Ar¹ represents phenyl substituted by one or two NO₂ groups or one to five (such as 2, 3, or 4) halogen groups, or a combination thereof.

In certain embodiments of compounds of the present disclosure Ar¹ is di-nitrophenyl or di-halophenyl, for example:
  3,5-di-chlorophenyl, 3,4-di-chlorophenyl, 2,4-di-chlorophenyl, 3,5-di-fluorophenyl,
  3,4-di-fluorophenyl or 2,4-di-fluorophenyl, or
  3,5-di-nitrophenyl, 3,4-di-nitrophenyl or 2,4-di-nitrophenyl.

In one embodiment the compound is V15F Actagardine (3,5-dichlorobenzylamine) monocarboxamide. V15F represents the position where the core structure of the compound of the invention differs from the core structure of the compound of formula (I) as drawn. In particular valine at position 15 is phenylalanine in this specific compound of the invention.

In one embodiment the amino acid at any one of 0, 2, 3, 4, 5, 8, 10, 11, 13, 15, 16 or 18 is selected from an amino acid for the give position listed in Table 1 or Table 4 below.

In one embodiment at least two amino acids at two or more positions selected from 0, 2, 3, 4, 5, 8, 10, 11, 13, 15, 16 are 18 are selected from an amino acid for the given position listed in Table 1 or Table 4 below.

In one embodiment the compound of formula (I) according to the disclosure has Ile at position 5 and Phe at position 15.

In one embodiment there is provided a compound comprising the peptide:

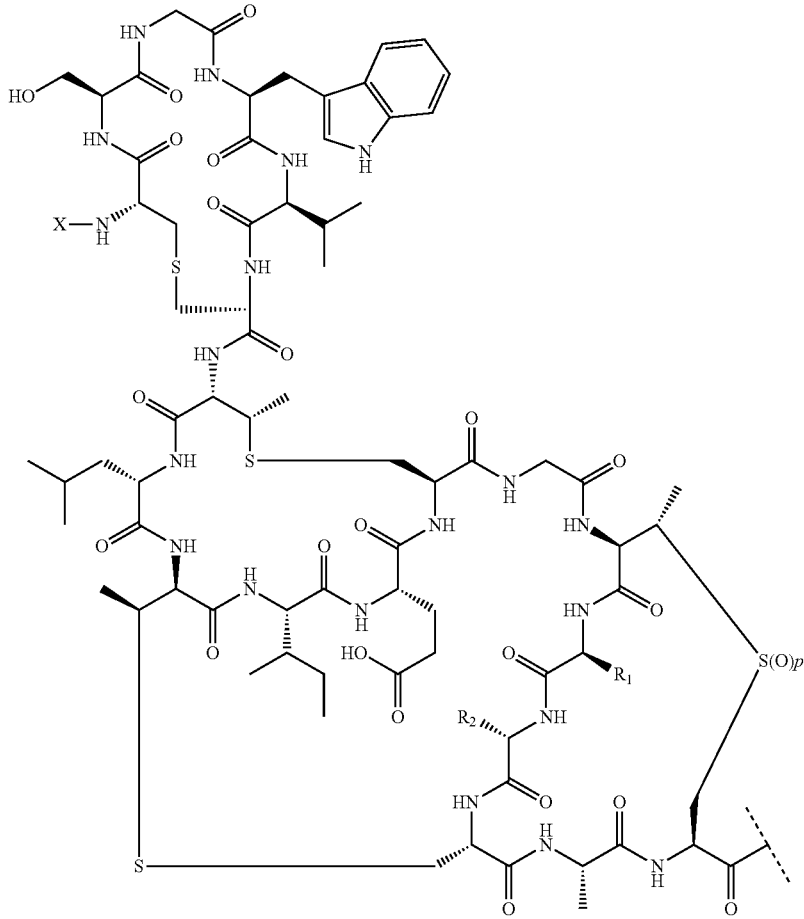

wherein:

X represents H or Ala;

p is 0 or 1;

R$^1$ represents —CH(CH$_3$)$_2$ or —CH$_2$CH(CH$_3$)$_2$;

R$^2$ represents —CH(CH$_3$)CH$_2$CH$_3$ or —CH(CH$_3$)$_2$;

wherein one or more amino acids at position 2, 3, 4, 5, 8, 10, 11, 13, 15, 16 or 18 in the compound of formula (I) have been replaced by an alternative amino acid, the proviso that when the amino acids are unchanged at positions 2, 3, 4, 5, 8, 10, 11, 13 and 18, and X is selected from H, Ala, Lys and Ile, and p is 1 positions 15 and 16 are not Val, Ile respectively, or X is selected from H and Ala, and p is 0 positions 15 and 16 are not Val, Ile respectively, or X is selected from H and Ala, and p is 1 positions 15 and 16 are not Leu, Val; Val, Val or Leu, Ile respectively, or X is selected from H, Ala, Ile, Phe, Val, Lys and Trp and p is 0 positions 15 and 16 are not Leu, Val respectively.

The broken line in the structure supra is across the bond through with the peptide is joined to the remainder of the molecule/entity.

The compounds of the present disclosure may be in the form of and/or may be administered as a pharmaceutically acceptable salt. For a review on suitable salts see Berge et al., J. Pharm. ScL, 1977, 66, 1-19.

Typically, a pharmaceutically acceptable salt may be readily prepared by using a desired acid or base as appropriate. The salt may precipitate from solution and be collected by filtration or may be recovered by evaporation of the solvent, for example, a compound of formula (I) may be dissolved in a suitable solvent, for example an alcohol such as methanol, and the acid may be added in the same solvent or another suitable solvent. The resulting acid addition salt may then be precipitated directly, or by addition of a less polar solvent such as diisopropyl ether or hexane, and isolated by filtration.

The skilled person will appreciate that where the compound of formula (I) contains more than one basic group. Thus bis salts or tris salts may also be formed and are salts according to the present disclosure.

Suitable salts are formed from inorganic or organic acids which form non-toxic salts include: lactobionate, mandelate (including (S)-(+)-mandelate, (R)-(−)-mandelate and (R,S)-mandelate), hydrochloride, hydrobromide, hydroiodide, sulfate, bisulfate, nitrate, phosphate, hydrogen phosphate, glutamate, acetate, trifluoroacetate, maleate, malate, fumarate, lactate, tartrate, citrate, formate, gluconate, succinate, ethyl succinate (4-ethoxy-4-oxo-butanoate), pyruvate, oxalate, oxaloacetate, saccharate, benzoate, glucolate, glucurinate, alkyl or aryl sulphonates (eg methanesulphonate, ethanesulphonate, benzenesulphonate or p-toluenesulphonate), mesylate and isethionate.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the herein are within the scope of the disclosure. The salts of the compound of the invention may form solvates (e.g. hydrates) and the disclosure also includes all such solvates.

The term "prodrug" as used herein means a compound which is converted within the body, e.g. by hydrolysis in the blood, into its active form that has medical effects. Pharmaceutically acceptable prodrugs are described in T. Higuchi and V. Stella, "Prodrugs as Novel Delivery Systems", Vol. 14 of the A.C.S. Symposium Series; Edward B. Roche, ed., "Bioreversible Carriers in Drug Design", American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of the disclosure in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of formula disclosure. Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

References hereinafter to a compound according to the disclosure include both compounds of the disclosure and their pharmaceutically acceptable salts and derivatives, such as solvates.

With regard to stereoisomers, the compounds of the disclosure have more than one asymmetric carbon atom. In the general formula of compounds herein as drawn, the solid wedge shaped bond indicates that the bond is above the plane of the paper. The broken bond indicates that the bond is below the plane of the paper.

It will be appreciated that the substituents in compounds of the disclosure may also have one or more asymmetric carbon atoms.

The compounds of the disclosure may occur as individual enantiomers or diastereomers. All such isomeric forms are included within the present disclosure, including mixtures thereof.

Generally separation of diastereoisomers or cis and trans isomers may be achieved by conventional techniques, e.g. by fractional crystallisation, chromatography or HPLC.

Compounds of described herein also extend to tautomeric forms thereof, for example, keto/enol tautomers.

The compounds of the disclosure may be in crystalline or amorphous form. Furthermore, crystalline forms of the compounds may exist as polymorphs, all forms are included in the present disclosure.

In another aspect, the invention provides a pharmaceutical composition comprising, as active ingredient, a compound of the disclosure or a pharmaceutically acceptable derivative thereof in association with a pharmaceutically acceptable excipient, diluent and/or carrier for use in therapy, and in particular, in the treatment of human or animal subjects suffering from a condition susceptible to amelioration by an antimicrobial compound.

In another aspect, the invention provides a pharmaceutical composition comprising a therapeutically effective amount of a compound of the present disclosure and a pharmaceutically acceptable excipient, diluent and/or carrier (including combinations thereof).

There is further provided by the present disclosure a process of preparing a pharmaceutical composition, which process comprises mixing a compound of the disclosure or a pharmaceutically acceptable derivative thereof, together with a pharmaceutically acceptable excipient, diluent and/or carrier.

The compounds of the disclosure may be formulated for administration in any convenient way for use in human or veterinary medicine and the disclosure therefore includes within its scope pharmaceutical compositions comprising a compound of the disclosure adapted for use in human or veterinary medicine. Such compositions may be presented for use in a conventional manner with the aid of one or more suitable excipients, diluents and/or carriers. Acceptable excipients, diluents and carriers for therapeutic use are well known in the pharmaceutical art, and are described, for example, in Remington's Pharmaceutical Sciences, Mack Publishing Co. (A. R. Gennaro edit. 1985). The choice of pharmaceutical excipient, diluent and/or carrier can be selected with regard to the intended route of administration and standard pharmaceutical practice. The pharmaceutical compositions may comprise as the excipient, diluent and/or carrier (or in addition to the excipient, diluent and/or carrier) any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

For some embodiments, the agents of the present disclosure may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO 91/11172, WO 94/02518 and WO 98/55148.

The compounds of the disclosure may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

The routes for administration (delivery) include, but are not limited to, one or more of: oral (e.g. as a dry powder/free flowing particulate formulation, tablet, capsule, or as an ingestable solution or suspension) rectal, buccal, and sublingual. The compositions of the disclosure include those in a form especially formulated for parenteral, oral, buccal, rectal, topical, implant, ophthalmic, nasal or genito-urinary use. In one aspect of the invention, the agents are delivered orally, hence, the agent is in a form that is suitable for oral delivery.

In some instances it may be possible to deliver the compounds of the disclosure by:

Intradermal delivery, topical delivery, including transdermal mucosal (e.g. as a nasal spray or aerosol for inhalation), nasal, gastrointestinal, intrauterine, intraurethrally and ophthalmical delivery, and parenterally (e.g. by an injectable form) including intraspinal, intraperitoneal, intramuscular, intravenous, intraarterially, intraventricularly, intraocular, intrasternally intracranial, intratracheal, intracerebroventricular, intracerebral, intrathecally subcutaneous, intravitreal, intracameral.

There may be different composition/formulation requirements depending on the different delivery routes/systems. By way of example, the pharmaceutical composition of the present disclosure may be formulated to be delivered using a mini-pump or by a mucosal route, for example, as a nasal spray or aerosol for inhalation or ingestable solution, or parenterally where the composition is formulated in an injectable form, for delivery by, for example, an intravenous, intramuscular or subcutaneous route. Alternatively, the formulation may be designed to be delivered by both routes.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents.

The compounds of the disclosure can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the disclosure may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents.

Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, calcium sulphate, dibasic calcium phosphate and glycine, mannitol, pregelatinised starch, corn starch, potato starch, disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Solid compositions of a similar type may also be employed as fillers in gelatin or HPMC (hydroxypropyl methylcellulose) capsules. Suitable, excipients in this regard include microcrystalline cellulose, lactose, calcium carbonate, calcium sulphate, dibasic calcium phosphate and, mannitol, pregelatinised starch, corn starch, potato starch or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Capsules, may be filled with a powder (of medicament alone or as blend with selected filler(s)) or alternatively a liquid, each comprising one or more compounds of formula (I) and a carrier. Where the capsule is filled with a powder the compounds of formula (I) and/or the carrier may be milled or micronised to provide material with an appropriate particle size.

Compounds of the disclosure may be coated, for example with as an enteric coating when administered orally as a tablet or capsule. The tablet or capsule, as appropriate, may, for example be coated by a thin film such as a EUDRAGIT® film available from Rohm Pharma Polymers, which allows controlled dissolution in the gastrointestinal tract. The films are available as cationic polymers such as EUDRAGIT® E 100 (aminoalkyl methacylate copolymers) or as anionic acrylic polymers such as EUDRAGIT® L (methacrylic acid copolymers) and EUDRAGIT S.

Permeable acrylic polymers such as EUDRAGIT® RL (amino methacrylate copolymer) and EUDRAGIT® RS are also available.

These coating formulations may be prepared as an aqueous dispersion including optional ingredients such as talc, silicone antifoam emulsion, polyethylene glycol. Alternatively the coating formulation may be prepared as an organic polymer solution.

Alternatively, tablets may be coated using OPADRY® (Surelease®) coating systems, available from Colorcon. Aqueous systems generally comprise up to 15% w/w of OPADRY®. Organic solvent systems generally comprise up to 5% w/w of OPADRY®.

The coatings may be prepared by known techniques, for example by:
1. weighing the required quantity of OPADRY® film coating system,
2. weighing the required quantity of water or other solvent(s) into a mixing vessel,
3. with a mixing propeller in the centre of the vessel and as close to the bottom of the vessel as possible, stirring the solvents to form a vortex without drawing air into the liquid,
4. steadily and quickly adding the OPADRY® powder to the vortex, avoiding powder flotation on the liquid surface,
5. increasing the stirrer speed in order to maintain the vortex, if required, and
6. after all the powder ingredients have been added, reducing the mixer speed and continuing mixing for approximately 45 minutes.

Coatings can be applied by known techniques, using tablet coating machines.

The thickness of the coating applied is generally in the range 5 to 35 microns such as 10 to 30 microns, more specifically 10 or 20 microns, depending on the required effect.

Alternatively, the tablet or a capsule, as appropriate, may be filled into another capsule (preferably a HPMC capsule such as Capsugel®) to provide either a tablet in capsule or capsule in capsule configuration, which when administered to a patient yields controlled dissolution in the gastrointestinal tract thereby providing a similar effect to an enteric coating.

Thus in one aspect the disclosure provides a solid dose formulation of a compound of the disclosure, for example where the formulation has an enteric coating.

In another aspect the disclosure provides a solid dose formulation comprising a protective capsule as outer layer, for example as a tablet in a capsule or a capsule in a capsule. The enteric coating may provide an improved stability profile over uncoated formulations.

Having said this it is believed that the compounds of the disclosure are not particularly susceptible to degradation by stomach acid or intestinal enzymes in vivo.

The compounds of the disclosure may also be administered orally, in veterinary medicine, in the form of a liquid drench such as a solution, suspension or dispersion of the active ingredient together with a pharmaceutically acceptable carrier or excipient.

For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The compounds of the invention may also, for example, be formulated as suppositories e.g. containing conventional suppository bases for use in human or veterinary medicine or as pessaries e.g. containing conventional pessary bases.

In one embodiment the formulation is provided as a formulation for topical administration including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are preferably used, the use of lactose or glucose, particularly but not exclusively in the form of their hydrates.

Particles for deposition in the lung require a particle size less than 10 microns, such as 1-9 microns suitably from 0.1 to 5 μm, particularly preferably from 1 to 5 μm. The particle size may be the size of the active component (i.e. the compound according to the disclosure).

The propellant gases which can be used to prepare the inhalable aerosols are known from the prior art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The above-mentioned propellent gases may be used on their own or in mixtures thereof.

Particularly suitable propellant gases are halogenated alkane derivatives selected from among TG11, TG 12, TG 134a and TG227. Of the abovementioned halogenated hydrocarbons, TG134a (1,1,1,2-tetrafluoroethane) and TG227 (1,1,1,2,3,3,3-heptafluoro propane) and mixtures thereof are suitable for use in formulations of the present invention.

The propellant-gas-containing inhalable aerosols may also contain other ingredients such as co-solvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the disclosure may contain, for example, 0.002 to 5% by weight, 0.01 to 3% by weight, 0.015 to 2% by weight, 0.1 to 2% by weight, 0.5 to 2% by weight or 0.5 to 1% by weight of active.

The compounds of the disclosure may also be used in combination with other therapeutic agents. The disclosure thus provides, in a further aspect, a combination comprising a compound of the disclosure or a pharmaceutically acceptable derivative thereof together with a further therapeutic agent. The combination may, for example be a combination of a compound of the disclosure and, for example an antibiotic, such as vancomycin, a beta-lactam (such as a cephalosporin), an aminoglycoside, a macrolide, a tetracyline, and/or an anti-inflammatory such as a steroid. The combination may be provided as a co-formulation or simply packaged together as separate formulations, for simultaneous or sequential delivery.

It is to be understood that not all of the compounds of the combination need be administered by the same route. Thus, if the therapy comprises more than one active component, then those components may be administered by different routes.

Thus the individual components of such combinations may be administered either sequentially or simultaneously in separate or combined pharmaceutical formulations by any convenient route.

When administration is sequential, either the compound of the disclosure or the second therapeutic agent may be administered first. When administration is simultaneous, the combination may be administered either in the same or a different pharmaceutical composition.

The combinations referred to above may conveniently be presented for use in the form of a pharmaceutical formulation and thus pharmaceutical formulations comprising a combination as defined above together with a pharmaceutically acceptable carrier or excipient comprise a further aspect of the disclosure.

When combined in the same formulation it will be appreciated that the two compounds must be stable and compatible with each other and the other components of the formulation. When formulated separately they may be provided in any convenient formulation, in such manner as are known for such compounds in the art.

The compositions may contain from 0.01-99% of the active material. For topical administration, for example, the composition will generally contain from 0.01-10%, more preferably 0.01-1% of the active material.

When a compound of the disclosure or a pharmaceutically acceptable derivative thereof is used in combination with a second therapeutic agent active against the same disease state the dose of each compound may be the same or differ from that employed when the compound is used alone. Appropriate doses will be readily appreciated by those skilled in the art. It will also be appreciated that the amount of a compound of the disclosure required for use in treatment will vary with the nature of the condition being treated and the age and the condition of the patient and will be ultimately at the discretion of the attendant physician or veterinarian.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

For oral and parenteral administration to humans, the daily dosage level of the agent may be in single or divided doses.

For systemic administration the daily dose as employed for adult human treatment it will range from 2-100 mg/Kg body weight, preferably 5-60 mg/Kg body weight, which may be administered in 1 to 4 daily doses. When the composition comprises dosage units, each unit will preferably contain 100 mg to 1 g of active ingredient. The duration of treatment will be dictated by the rate of response.

In one embodiment the treatment regime is continued for 1, 2, 3, 4, 5, 6, 7, 8, 9, 10, 11, 12, 13, 14, 15, 16, 17, 18, 19, 20, 21 or more days.

As described above, the compounds of the present disclosure may be employed in the treatment or prophylaxis of humans and/or animals.

In one embodiment a compound of the disclosure is useful in the treatment of skin infections, in particular bacterial skin and soft tissue infection.

In one aspect, the disclosure provides use of a compound of the disclosure in therapy, for example, for treatment of microbial infections such as bacteraemia, pneumonia and microbial infection of soft tissue including surgical wounds, in particular staphylococcal infections including MRSA infection.

In one embodiment the compounds of the disclosure are useful for the treatment of enterococcal infections including *Enterococcus faecalis* and *E. faecium* infection, for example skin and skin structure infections, endocarditis, urinary tract infection and sepsis.

In one embodiment the compounds of the disclosure are useful for the treatment of *Streptococcus pyogenes*, for example skin infections such as impetigo, erysipelas and cellulitis, throat infections, scarlet fever, and acute glomerulonephritis.

In one embodiment compounds of the disclosure are useful in the treatment of *Streptococcus pneumoniae* infection, for example pnuemonia, acute sinusitus, otitis media, meningitis, bacteremia, osteomylitis, septic arthritis and endocarditis.

In one aspect the compounds of the disclosure are employed for controlling bacterial overgrowth syndrome. Overgrowth syndrome (BOS) occurs when the normally low bacterial colonization in the upper GI tract and/or lower intestines significantly increases.

In one aspect, the disclosure provides use of a compound of the disclosure in therapy, for example, for treatment of microbial infections such as *Clostridium difficile* infection, in particular diarrhea associated therewith, or one or more microbial infections described herein, particularly by oral delivery of a compound of the disclosure.

In one aspect, the disclosure provides use of a compound of the disclosure in therapy, for example, for treatment of microbial infections such as *Micrococcus luteus* infection.

In one aspect there is provided use of a compound of the disclosure for the prophylaxis, treatment or maintenance of IBS (irritable bowel syndrome). See for example Rifaximin Treatment for Symptoms of Irritable Bowel Syndrome. Andrea L. Fumi and Katherine Trexler, *The Annals of Pharmacotherap*, 2008, 4, 408.

In one embodiment a compound of the disclosure is useful in the treatment of ulcerative colitis including prophylactic treatment to prevent recurrence thereof. The compounds may be particularly suitable for the treatment of steroid refractory ulcerative colitis. See for example steroid-refractory ulcerative colitis treated with corticosteroids, metronidazole and vancomycin: a case report J. Miner, M. M Gillan, P. Alex, M Centola, *BMC Gastroenterology* 2005, 5:3.

The compounds of the present disclosure may be particularly useful for long term treatment.

In one aspect there is provided a compound of the disclosure or a composition comprising same for use in treatment or prophylaxis for example the treatment or prophylaxis of any one the indications described herein.

In one aspect there is provided a compound of the disclosure or a composition comprising the same for the manufacture of a medicament for one or more of the indications defined above.

In one aspect there is provided a method of treatment comprising the step of administering a therapeutically effective amount of a compound of the disclosure or a pharmaceutical composition containing the same to a patient (human or animal) in need thereof, for example for the treatment of an infection/illness or disease as described herein.

In the context of this specification "comprising" is to be interpreted as "including". Aspects of the invention comprising certain elements are also intended to extend to alternative embodiments "consisting" or "consisting essentially" of the relevant elements.

Where technically appropriate embodiments may be combined and thus the disclosure extends to all permutations/combinations of the embodiments provided herein.

Preferences given for compounds of formula (I) may equally apply to other compounds of the invention, disclosed herein, as technically appropriate.

Site directed mutagenesis of the gene encoding actagardine may be performed using methods known per se in the art. An expression vector and host for production of actagardine variants has been described (Boakes et al., 2009). Annealed oligonucleotides encoding actagardine variants were introduced into this expression vector and delivered to the host organism. Using this methodology the LanO gene can be silenced to generate deoxyactagardine variants. The methodology can also readily be employed to generate actagardine B and deoxyactagardine B type variants. Thus the starting point for mutation, may for example be actagardine, actagardine B, deoxyactagardine, deoxyactagardine or other lantibiotoc nucleotide sequence. Once the sequence has been manipulated to encode the desired core it can be inserted into any suitable host for expression.

Thus in one embodiment there is provide a method comprising the steps of generating a nucleotide sequence encoding peptide of formula (I) wherein $R^3$ represents —OH or an amino acid.

The method may further comprise (or may alternatively comprise) the step of expressing the nucleotide sequence in a suitable host, for example *Actinoplanes garbadinensis*.

In one embodiment the method according to the present disclosure comprises the step of performing synthetic organic chemistry on the peptide, expressed from the host, to provide a semisynthetic derivate of the peptide.

EXAMPLES

Production of Actagardine Variants

Using the method described above the obtained mutants produced variant molecules of actagardine. Agar plugs containing the mutants were used to inoculate miniaturised culture vessels containing 7 mL of AAS seed medium (soluble starch 10 g, glucose 10 g, Bacto-peptone 5 g, dry corn steep liquor 1 g, yeast extract 2 g, water to 1 liter and pH adjusted to 7) supplemented with apramycin and nalidixic acid, both to a final concentration of 50 µg/mL. The cultures were incubated at 30° C. and 200 rpm for 96 h after which 0.350 ml (5%) from each was used to inoculate a miniaturised culture vessels containing 7 ml of GM1 (meat extract 4 g, peptone 4 g, NaCl 2.5 g, yeast extract 1 g, soya flour 10 g, glucose 25 g, $CaCO_3$ 5 g, water to 1 liter and pH adjusted to 7.6). The cultures were incubated at 30° C. and 200 rpm. Following 7 days incubation, cells were removed from fermentation broth by centrifugation and the supernatants then analysed by high performance liquid chromatography (HPLC) and HPLC-mass spectrometry (HPLC-MS). HPLC-MS analyses were performed on a Hewlett Packard 1050 series HPLC system linked to a Micromass Platform LC (operated with MassLynx version 3.5 software) with the following parameters

| | |
|---|---|
| Column | Agilent Zorbax SB-C18 150 × 4.6 mm 5µ |
| Mobile Phase A | 10% acetonitrile, 0.1% formic acid, in water |
| Mobile Phase B | 90% acetonitrile, 0.1% formic acid, in water |
| Flow rate | 1 ml/min |
| Gradient | |
| Time 0 min | 100% A |
| Time 10 min | 0% A |
| Time 11 min | 0% A |
| Time 11.2 min | 100% A |
| Cycle time | 15 min |
| Wavelength | 200-400 nm |
| Injection volume | 10 µl |
| Post column split | 1:10 |
| Mass spectrometer | Micromass Platform LC |
| Mode | Electrospray positive ion |
| Cone voltage | 40 V |
| Capillary voltage | 3.10 V |
| Skimmer lens offset | 5 V |
| Ion Energy | 1.4 V |

Actagardine variants produced by site directed mutagenesis are set out in Table 1:

TABLE 1

Actagardine single point variants produced by fermentation of actagardine mutants

| Position | Number of variants prepared for each position and amino acid changes at any given position |
|---|---|
| 0 (ala) | Gly, His, Asn, Gln, Ser, Thr |
| 2 (ser) | Ala, Asp*, Glu, Gly, Ile, Asn, Gln, Thr, Val |
| 3 (gly) | Ala, Ser |
| 4 (trp) | Phe, His |
| 5 (val) | Ala, Glu, Phe**, Ile, Leu, Met*, Ser, Thr**, Trp* |
| 8 (leu) | Phe, Ile, Met, Val |
| 10 (ile) | Phe, His, Leu, Met, Thr, Ser, Val |
| 11 (glu) | Asp |
| 13 (gly) | Ala, Ser |
| 15 (val) | Ala, Phe, Gly, His**, Ile, Leu, Met, Gln**, Arg**, Thr, Trp* |
| 16 (ile) | Phe, Leu, Met*, Asn, Gln, Ser, Thr, Dhb* |
| 18 (ala) | Gly, Ile, Asn, Ser, Thr, Val |

*ala(0) variant only,
**variant + ala(0)variant

Example 1

A0G Actagardine (ala 0 gly).

Example 2

A0H Actagardine (ala 0 his).

Example 3

A0N Actagardine (ala 0 asn).

Example 4

A0Q Actagardine (ala 0 gln).

Example 5

A0S Actagardine (ala 0 ser).

Example 6

A0T Actagardine (ala 0 thr).

Example 7

S2A Actagardine (ser 2 ala).

Example 8

S2D Actagardine (ser 2 asp).

Example 8

S2E Actagardine (ser 2 glu).

Example 10

S2G Actagardine (ser 2 gly).

Example 11

S2I Actagardine (ser 2 ile).

Example 12

S2N Actagardine (ser 2 asn).

Example 13

S2Q Actagardine (ser 2 gln).

Example 14

S2T Actagardine (ser 2 thr).

Example 15

S2V Actagardine (ser 2 val).

Example 16

G3A Actagardine (gly 3 ala).

Example 17

G3S Actagardine (gly 3 ser).

Example 18

W4F Actagardine (trp 4 phe).

Example 19

W4H Actagardine (trp 4 his).

Example 20

V5A Actagardine (val 5 ala).

Example 21

V5E Actagardine (val 5 glu).

Example 22

V5F Actagardine (val 5 phe).

Example 23

V5I Actagardine (val 5 ile).

Example 24

V5L Actagardine (val 5 leu).

Example 25

V5M Actagardine (val 5 met).

Example 26

V5S Actagardine (val 5 ser).

Example 27

V5T Actagardine (val 5 thr).

Example 28

V5W Actagardine (val 5 trp).

Example 29

L8F Actagardine (leu 8 phe).

Example 30

L8I Actagardine (leu 8 ile).

Example 31

L8M Actagardine (leu 8 met).

Example 32

L8V Actagardine (leu 8 val).

Example 33

I10F Actagardine (ile 10 phe)

Example 34

I10H Actagardine (ile 10 his).

Example 35

I10L Actagardine (ile 10 leu)

Example 36

I10M Actagardine (ile 10 met).

Example 37

I10S Actagardine (ile 10 ser)

Example 38

I10T Actagardine (ile 10 thr).

Example 39

I10V Actagardine (ile 10 val).

Example 40

E11D Actagardine (glu 11 asp).

Example 41

G13A Actagardine (gly 13 ala).

Example 42

G13S Actagardine (gly 13 ser).

Example 43

V15A Actagardine (val 15 ala).

Example 44

V15F Actagardine (val 15 phe).

Example 45

V15G Actagardine (val 15 gly).

Example 46

V15H Actagardine (val 15 his).

Example 47

V15I Actagardine (val 15 ile).

Example 48

V15L Actagardine (val 15 leu).

Example 49

V15M Actagardine (val 15 met).

Example 50

V15Q Actagardine (val 15 gln).

Example 51

V15R Actagardine (val 15 arg).

Example 52

V15T Actagardine (val 15 thr).

Example 53

V15W Actagardine (val 15 trp).

Example 54

I16F Actagardine (ile 16 phe).

Example 55

I16L Actagardine (ile 16 leu).

Example 56

I16M Actagardine (ile 16 met).

Example 57

I16N Actagardine (ile 16 asn).

Example 58

I12Q Actagardine (ile 16 gln).

Example 59

I12S Actagardine (ile 16 ser).

Example 60

I12T Actagardine (ile 16 thr).

Example 61

I16T Actagardine (ile 16 dhb).

Example 62

A12G Actagardine (ala 18 gly).

Example 63

A12I Actagardine (ala 18 ile).

Example 64

A18N Actagardine (ala 18 asn).

Example 65

A18S Actagardine (ala 18 ser).

Example 66

A19T Actagardine (ala 18 thr).

Example 67

A18V Actagardine (ala 18 val).

Example 68

V15F Actagardine (3,5-dichlorobenzylamine)monocarboxamide

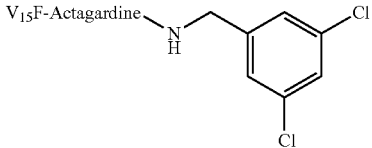

V15F Actagardine (20 mg), 3,5-dichlorobenzylamine (3.8 mg) and diisopropylethylamine (3.5 µL) were dissolved in dry dimethylformamide (0.2 mL). A solution of benzotriazole-1-yl-oxy-tris-pyrrolidino-phosphonium hexafluorophosphate (PyBOP) (8.4 mg) in dry dimethylformamide (2 mL) was added portionwise. The reaction was followed by analytical HPLC (See Table 2) and PyBOP was added until the starting material had been consumed.

TABLE 2

Analytical HPLC conditions for the separation of lantibiotic (e.g. actagardine, actagardine B, or deoxy-actagardine B) and derivatised products.

| Column: | Zorbax 5μ C18(2) 150 × 4.6 mm | | |
|---|---|---|---|
| Mobile Phase A: | 30% Acetonitrile in 20 mM potassium phosphate buffer pH 7.0 | | |
| Mobile Phase B: | 65% Acetonitrile in 20 mM potassium phosphate buffer pH 7.0 | | |
| Flow rate: | 1 mL/min | | |
| Gradient: | Time 0 min | 100% A | 0% B |
| | Time 10 min | 0% A | 100% B |
| | Time 11 min | 0% A | 100% B |
| | Time 11.2 min | 100% A | 0% B |
| | Cycle time 15 min | | |
| Injection volume: | 10 μL | | |
| Detection: | 210 nm | | |

The crude reaction mixture was poured into 30% aqueous methanol and the resulting solution was loaded on to a Varian Bond Elut C18 column (30 g). The column was then washed sequentially with 50%, 60%, 70%, 80%, 90% aqueous methanol, with most of the desired material eluting in the 70% fraction. Yield 39%. Calculated for [M+Na H]$^{+2}$ 1058.5. found 1059.

Samples were analysed by LC-MS using the conditions described in Table 3.

TABLE 3

LC/MS conditions for the analysis of lantibiotic (e.g. deoxy-actagardine B) and derivatised products.

| Column: | Zorbax 5μ C18(2) 150 × 4.6 mm | | |
|---|---|---|---|
| Mobile Phase A: | 10% acetonitrile, 0.1% formic acid | | |
| Mobile Phase B: | 90% acetonitrile, 0.1% formic acid | | |
| Flow rate: | 1 mL/min | | |
| Gradient: | Time 0 min | 100% A | 0% B |
| | Time 10 min | 0% A | 100% B |
| | Time 11 min | 0% A | 100% B |
| | Time 11.1 min | 100% A | 0% B |
| | Cycle time 15 min | | |
| Injection volume: | 20 μL | | |
| Mass Spectrometer parameters | | | |
| Ionisation | Electrospray +ve | | |
| Mass range | 250-1500mu | | |
| Capillary voltage | 3.10 KV | | |
| Cone voltage | 40 V | | |
| Skimmer lens offset | 5 V | | |
| Ion energy | 1.4 V | | |

The method of example 68 may be used to prepare the following V15F actagardine derivates wherein OH of the C-terminal is replaced with the fragment:

Example 69

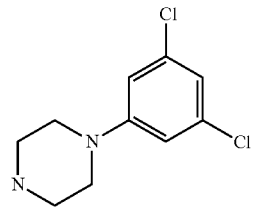 [SMILES: Clc1cc(Cl)cc(N2CCNCC2)c1]

Example 70

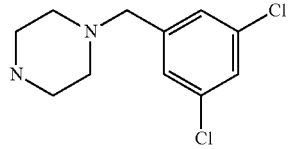 [SMILES: Clc1cc(Cl)cc(CN2CCNCC2)c1]

Example 71

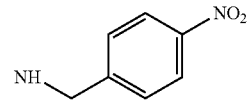 [SMILES: NCc1ccc([N+](=O)[O-])cc1]

Example 72

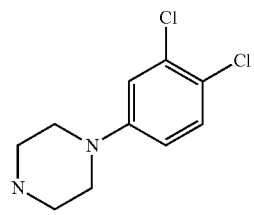 [SMILES: Clc1ccc(N2CCNCC2)cc1Cl]

Example 73

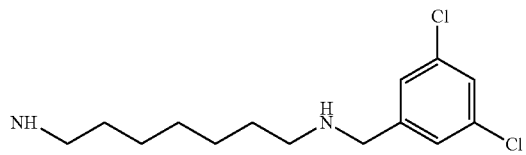 [SMILES: NCCCCCCCNCc1cc(Cl)cc(Cl)c1]

-continued
Example 74 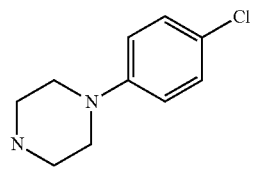 [SMILES: Clc1ccc(N2CCNCC2)cc1]
Example 75 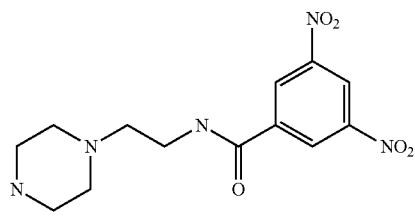 [SMILES: O=C(NCCN1CCNCC1)c1cc([N+](=O)[O-])cc([N+](=O)[O-])c1]
Example 76 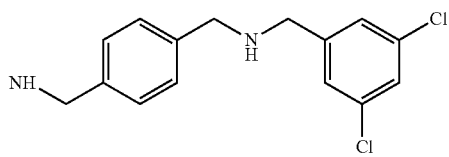 [SMILES: NCc1ccc(CNCc2cc(Cl)cc(Cl)c2)cc1]
Example 77 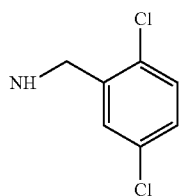
Example 78 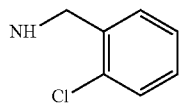
Example 79 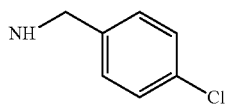
Example 80 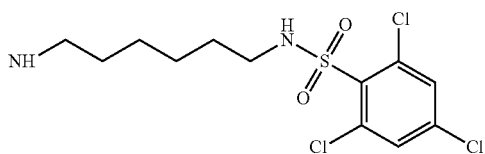 [SMILES: NCCCCCCNS(=O)(=O)c1c(Cl)cc(Cl)cc1Cl]
Example 81 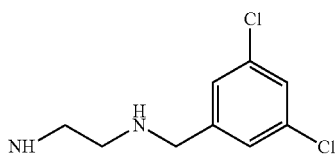 [SMILES: NCCNCc1cc(Cl)cc(Cl)c1]
Example 82 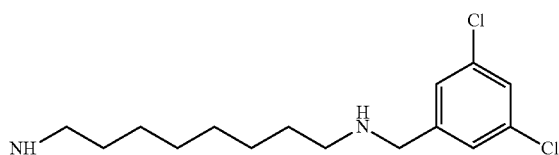 [SMILES: NCCCCCCCCNCc1cc(Cl)cc(Cl)c1]

-continued
| | |
|---|---|
| Example 83 | 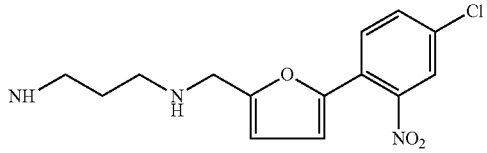 [SMILES: NCCCNCc1ccc(-c2ccc(Cl)cc2[N+](=O)[O-])o1] |
| Example 84 | 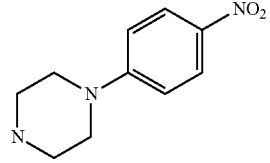 [SMILES: O=[N+]([O-])c1ccc(N2CCNCC2)cc1] |
| Example 85 | 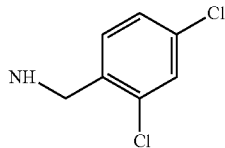 |
| Example 86 | 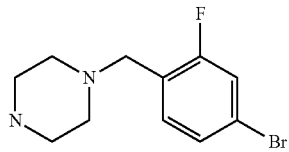 [SMILES: Fc1cc(Br)ccc1CN1CCNCC1] |
| Example 87 | 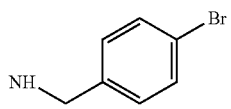 |
| Example 88 | 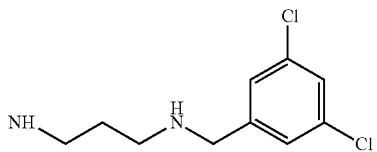 [SMILES: NCCCNCc1cc(Cl)cc(Cl)c1] |
| Example 89 | 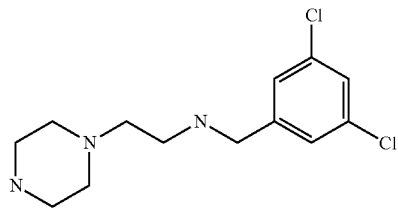 [SMILES: Clc1cc(Cl)cc(CNCCN2CCNCC2)c1] |
| Example 90 | 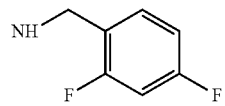 |
| Example 91 | 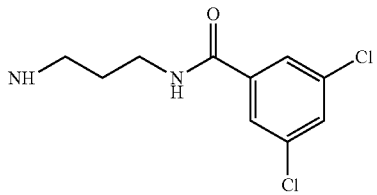 [SMILES: NCCCNC(=O)c1cc(Cl)cc(Cl)c1] |
| Example 92 | 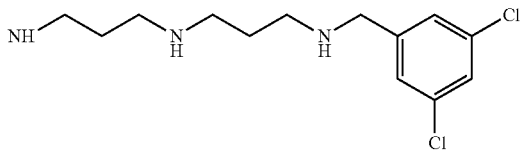 [SMILES: NCCCNCCCNCc1cc(Cl)cc(Cl)c1] |

Example 93
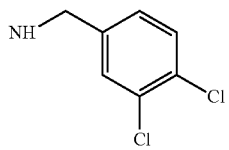

Example 94
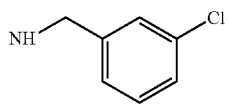

Example 95
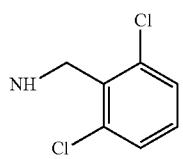

Example 96
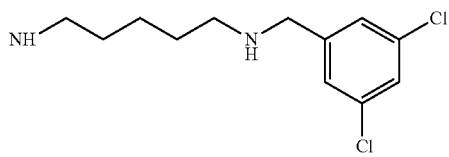 [SMILES: NCCCCCNCc1cc(Cl)cc(Cl)c1]

Example 97
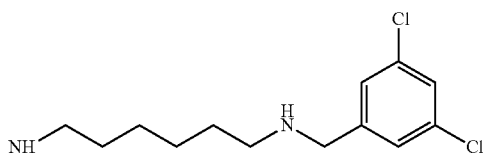 [SMILES: NCCCCCCNCc1cc(Cl)cc(Cl)c1]

Example 98
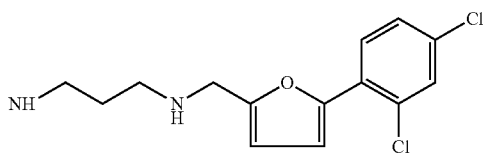 [SMILES: NCCCNCc1ccc(-c2ccc(Cl)cc2Cl)o1]

Example 99

V15F actagardine (7-amino-1-heptylamide monocarboxamide)

V15F actagardine B (2.5 g), 1,7-diaminoheptane (0.52 g) and diisopropylethylamine (0.44 ml) can be dissolved in dry dimethylformamide (10 mL). A solution of benzotriazole-1-yl-oxy-tris-pyrrolidino-phosphonium hexafluorophosphate (PyBOP) (1.04 g) in dry dimethylformamide (5 mL) may be added portionwise over 2 h. The reaction is followed by analytical hplc (See Table I) and PyBOP is added until the starting material had been consumed.

Example 100

V15F actagardine (2-amino-1-ethylamide monocarboxamide)

Can be prepared from V15F actagardine and 1,2-ethylenediamine employing the process described above for Example 99.

Example 101

V15F actagardine (5-amino-1-pentylamide monocarboxamide)

Can be prepared from V15F actagardine and 1,5-diaminopentane employing the process described above for Example 99.

Example 102

V15F actagardine (9-amino-1-nonylamide monocarboxamide)

Can be prepared from V15F actagardine and 1,9-diaminononane employing the process described above for Example 99.

Example 103

V15F actagardine (12-amino-1-dodecylamide monocarboxamide)

Can be prepared from V15F actagardine and 1,12-diaminododecane employing the process described above for Example 99

Example 104

Actagardine variants having antibacterial activity as determined by a bioassay using agar plates containing *Micrococcus luteus* ATCC 4698 as indicator strain were made. These variants are set out in Table 4:

TABLE 4

Actagardine variants active against *Micrococcus luteus* ATCC4698

| Position | Number of variants prepared for each position and amino acid changes at any given position |
|---|---|
| 0 (ala) | His, Asn, Gln, Ser, Thr |
| 2 (ser) | Ala, Gly, Ile, Asn, Gln, Thr, Val |
| 5 (val) | Phe, Ile, Leu, Met |
| 8 (leu) | Phe, Ile, Met, Val |
| 10 (ile) | Leu, Met, Thr, Val |
| 13 (gly) | Ala, Ser |
| 15 (val) | Ala, Phe, Ile, Leu, Met, Trp |
| 16 (ile) | Phe, Leu, Met |
| 18 (ala) | Gly, Asn, Ser, Thr, Val |

Example 105

MIC Data for Isolated Actagardine Variants

A selection of variants produced in Example 104 above, were tested further for activity against *Clostridium difficile* 630. Glycerol suspensions containing the mutants were used to inoculate 2×250 ml flasks containing 50 mL of AAS seed medium (soluble starch 10 g, glucose 10 g, Bacto-peptone 5 g, dry corn steep liquor 1 g, yeast extract 2 g, water to 1 liter and pH adjusted to 7) supplemented with apramycin to a final concentration of 50 µg/mL. The cultures were incubated at 30° C. and 200 rpm for 96 h after which 25 ml (5%) from each was used to inoculate 4×2 liter flasks containing 500 ml of GM1 (meat extract 4 g, peptone 4 g, NaCl 2.5 g, yeast extract 1 g, soyflour 10 g, glucose 25 g, $CaCO_3$ 5 g, water to 1 liter and pH adjusted to 7.6). The cultures were incubated at 30° C. and 200 rpm. Following 7 days incubation, cells were removed from fermentation broth by centrifugation and the supernatant then analysed by high performance liquid chromatography (HPLC) and HPLC-mass spectrometry (HPLC-MS). The HPLC analyses were performed using a Hewlett Packard 1050 series HPLC system with an Agilent Zorbax SB-C18, 4.6×150 mm, 5µ column. The HPLC-MS analyses were performed on a HPLC system (as described) linked to a Micromass Platform LC operated with MassLynx version 3.5 software.

Actagardine variants were captured from aqueous broth samples by absorption onto Diaion HP-20 resin. Aqueous broth was removed from Diaion HP20 resin by filtration. The resin was then washed with approximately 4 bed volumes of water followed by 4 bed volumes of 25% methanol. The respective compound was eluted from Diaion HP-20 resin using 5 to 10 bed volumes of 75% methanol. The 75% methanol fraction containing the actagardine variant was concentrated by evaporation to approximately a third of the starting volume. The concentrate was then diluted with an equal volume of water and the resulting solution was loaded onto a 10 g Varian Bond Elute C18 cartridge that had been pre-equilibrated with methanol and then water. The C18 cartridge was then washed with 2 column volumes of water followed by 2 column volumes of 30% methanol. The compound was eluted from the C18 cartridge using 3 column volumes of methanol containing 0.5% formic acid. The fraction containing DAB or actagardine B was concentrated by evaporation. The respective lantibiotic was then purified by preparative HPLC using the following parameters.

| | |
|---|---|
| Column | Capital HPLC Ltd, C18 BDS, HL5, 15 cm × 20 mm |
| Mobile Phase A | 30% Acetonitrile in 20 mM Potassium Phosphate pH 5.0 |
| Mobile Phase B | 65% Acetonitrile in 20 mM Potassium Phosphate pH 5.0 |
| Flow Rate | 10 ml/min |
| Gradient | |
| Time 0 min | 100% A |
| Time 1 min | 100% A |
| Time 29 min | 65% A |
| Time 30 min | 0% A |
| Time 33 min | 0% A |
| Time 34 min | 100% A |
| Cycle time | 35 min |
| Detection | 210 nm |

Preparative HPLC fractions that contained the purified actagardine variant were pooled and concentrated by evaporation. The sample was desalted by applying the concentrate to a 10 g Varian Bond Elute C18 cartridge that had been pre-equilibrated with methanol and then water. The C18 cartridge was then washed with 2 column volumes of water followed by 2 column volumes of 30% methanol. The actagardine variant was eluted from the C18 cartridge using 3 column volumes of methanol containing 0.5% formic acid. The purified actagardine variant was then evaporated to dryness.

Minimum inhibitory concentrations (MICs) were determined by two-fold serial antibiotic dilutions in Wilkins-Chalgren Anaerobe agar under anaerobic conditions. *C. difficile* 630 cultures were inoculated onto pre-reduced Braziers (C.C.E.Y.) agar plates and grown at 37° C. for 48 hours under anaerobic conditions. Two to three colonies of the 48 hours cultures were inoculated into 5 ml of pre-reduced Schaedlers Broth and grown at 37° C. for 24 hours under anaerobic conditions. This culture was diluted with pre-reduced 0.9% NaCl to achieve the turbidity of the 0.5 McFarland standard and applied to the antibiotic containing plates at a final inoculum of $10^5$ cfu/spot. The plates were incubated in an anaerobic chamber at 37° C. for 48 h and examined for growth. Vancomycin was used as a reference antibiotic for quality control. The MIC was the lowest concentration of antibiotic that completely inhibited growth or caused markedly reduction of growth as compared to growth on drug-free plates.

The results for the actagardine variants A0N, A0Q, A0H, S2A, S2G, S2Q, S2T, V5I, I10M, V15F, V15I, I16F, I16L, A18G, A18S and A18V are set out in Table 5.

TABLE 5

MIC against *Clostridium difficile* 630

| Compound | MIC (µg/mL) |
|---|---|
| Actagardine | 8 |
| A0N | 4, 8 |
| A0Q | 4, 8 |
| A0H | 4 |
| S2A | 4 |
| S2G | 8 |
| S2Q | >8 |
| S2T | 8 |
| V5I | 2, 4 |
| I10M | >8 |
| V15F | 2, 4 |

TABLE 5-continued

MIC against *Clostridium difficile* 630

| Compound | MIC (μg/mL) |
|---|---|
| V15I | 4 |
| I16F | 8, >8 |
| I16L | >8 |
| A18G | 8 |
| A18S | 8, >8 |
| A18V | >8 |

The invention claimed is:

1. A compound of formula (I):

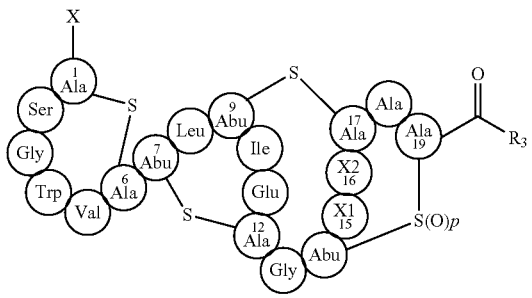

wherein:
X is H or an amino acid;
p is 0 or 1;
X1 is —CH(CH$_3$)$_2$ or —CH$_2$CH(CH$_3$)$_2$;
X2 is —CH(CH$_3$)CH$_2$CH$_3$ or —CH(CH$_3$)$_2$;
R$_3$ is —OH or —ZNR$^4$R$^5$;
Z is a bond or an amino acid;
R$^4$ is hydrogen, or a C$_{1-10}$ branched or unbranched alkyl chain wherein one, two or three carbon atoms are optionally replaced by a heteroatom and the alkyl chain optionally bears 1 or 2 oxo substituents and/or optionally bears one 5- to 6-membered heterocyclyl;
R$^5$ is hydrogen, —R$^A$-L-Ar$^1$ or a C$_{1-10}$ branched or unbranched alkyl chain wherein one, two or three carbon atoms are optionally replaced by a heteroatom and the alkyl chain optionally bears 1 or 2 oxo substituents and/or optionally bears one 5- to 6-membered heterocyclyl, or
R$^4$ together with R$^5$ and the nitrogen to which they are attached form a 5- or 6-membered heterocyclic group optionally including a further heteroatom selected from N, O or S, wherein the heterocyclic group is optionally substituted by:
a C$_{0-10}$ branched or unbranched alkyl chain wherein one, two or three carbon atoms are optionally replaced by a heteroatom and the alkyl chain optionally bears 1 or 2 oxo substituents, the alkyl chain optionally substituted by:
C$_{3-7}$ cycloalkyl;
5- to 6-membered heteroaryl;
5- to 6-membered heterocyclyl;
C$_{3-7}$ aryl;
YAr$^1$, or
wherein the heteraryl, heterocyclyl and aryl are optionally substituted by a C$_{1-10}$ branched or unbranched alkyl chain wherein one, two or three carbon atoms are optionally replaced by a heteroatom and the alkyl chain optionally bears 1 or 2 oxo substituents, or
C$_{3-7}$ cycloalkyl;
5- to 6-membered heteroaryl;
5- to 6-membered heterocyclyl;
C$_{3-7}$ aryl;
YAr$^1$, or
wherein the heteraryl, heterocyclyl and aryl are optionally substituted by a C$_{1-10}$ branched or unbranched alkyl chain wherein one, two or three carbon atoms are optionally replaced by a heteroatom and the alkyl chain optionally bears 1 or 2 oxo substituents;
R$^A$ is a bond, —C$_{0-9}$ alkylC$_{6-10}$aryl, —C$_{0-9}$ alkylC$_{5-11}$heteroaryl, —C$_{0-9}$ alkylC$_{3-6}$cycloalkyl, or —C$_{0-9}$ alkyl C$_{5-11}$heterocycle;
L is a straight or branched C$_{0-15}$ alkyl chain wherein optionally one, two or three carbon atoms are replaced by a heteroatom independently selected from N, O or S, wherein the chain is optionally substituted by one or more oxo or nitro groups, with the proviso that a replacement heteroatom is not bonded directly to the N of the group —NR$^3$R$^4$;
Y is a straight or branched C$_{0-15}$ alkyl chain wherein optionally one or more carbon atoms are replaced by a heteroatom independently selected from N, O or S, wherein the chain is optionally substituted by one or more oxo or nitro groups;
Ar$^1$ is phenyl substituted by one or two NO$_2$ groups or one to five halogen groups, or one or two C$_{1-3}$ haloalkyl groups, or a combination thereof, wherein the amino acid at position 15 and optionally 1, 2, or 3 amino acid(s) at position 2, 3, 4, 5, 8, 10, 11, 13, 16 or 18 in formula (I) includes replacement by an alternative amino acid, wherein
the replacement amino acid at position 2 is selected from the group consisting of Ala, Asp, Glu, Gly, Ile, Asn, Gln, Thr and Val;
the replacement amino acid at position 3 is selected from the group consisting of Ala and Ser;
the replacement amino acid at position 4 is selected from the group consisting of His and Phe;
the replacement amino acid at position 5 is selected from the group consisting of Ala, Glu, Phe, Ile, Leu, Met, Ser, Thr and Trp;
the replacement amino acid at position 8 is selected from the group consisting of Phe, Ile, Met and Val;
the replacement amino acid at position 10 is selected from the group consisting of Phe, His, Leu, Met, Ser, Thr and Val;
the replacement amino acid at position 11 is Asp;
the replacement amino acid at position 13 is selected from the group consisting of Ala and Ser;
the replacement amino acid at position 15 is selected from the group consisting of Ala, Phe, Gly, His, Ile, Met, Gln, Arg, Thr and Trp;
the replacement amino acid at position 16 is selected from the group consisting of Phe, Leu, Met, Asn, Gln, Ser, Thr and dehydrobutyrine; and
the replacement amino acid at position 18 is selected from the group consisting of Gly, Ile, Asn, Ser, Thr and Val;
with the proviso that when the amino acids are unchanged at positions 2, 3, 4, 5, 6, 10, 11, 13 and 18:
and X is selected from the group consisting of H, Ala, Lys and Ile, and p is 1, then positions 15 and 16 are not Val and Ile respectively;

and or X is selected from the group consisting of H and Ala, and p is 0, then positions 15 and 16 are not Val and Ile respectively;

or X is selected from the group consisting of H and Ala, and p is 1, then positions 15 and 16 are not Leu and Val; Val and Val; or Leu and Ile respectively;

or X is selected from the group consisting of H, Ala, Ile, Phe, Val, Lys and Trp, and p is 0, then positions 15 and 16 are not Leu and Val respectively;

and with the proviso that the compound is not V15F Actagardine (3,5-dichlorobenzylamine) monocarboxamide, and the compound is not V15F Actagardine.

2. The compound according to claim 1, wherein X is an amino acid selected from the group consisting of Phe, Gly, His, Asn Gln, Ser and Thr.

3. The compound according to claim 1, wherein the amino acid at position 2 is replaced.

4. The compound according to claim 1, wherein the amino acid at position 3 is replaced.

5. The compound according to claim 1, wherein the amino acid at position 4 is replaced.

6. The compound according to claim 1, wherein the amino acid at position 5 is replaced.

7. The compound according to claim 1, wherein the amino acid at position 8 is replaced.

8. The compound according to claim 1, wherein the amino acid at position 10 is replaced.

9. The compound according to claim 1, wherein the amino acid at position 11 is replaced.

10. The compound according to claim 1, wherein the amino acid at position 13 is replaced.

11. The compound according to claim 1, wherein the amino acid at position 16 is replaced.

12. The compound according to claim 1, wherein the amino acid at position 18 is replaced.

13. The compound according to claim 1, wherein $R_3$ is —OH.

14. The compound according to claim 1, wherein X is H.

15. The compound according to claim 1, wherein X is alanine.

16. The compound according to claim 1 wherein X is selected from the group consisting of Arg, His and Gln.

17. The compound according to claim 1 wherein the replacement amino acid at position 2 is selected from the group consisting of Ala, Gly and Thr.

18. The compound according to claim 1 wherein the replacement amino acid at position 5 is Ile.

19. The compound according to claim 1 wherein the replacement amino acid at position 15 is Phe.

20. The compound according to claim 1 wherein the replacement amino acid at position 18 is Gly.

21. The compound according to claim 1 wherein positions 15 and 16 are not any one of the following combinations: Val and Ile; Val and Val; Leu and Ile and Leu and Val, respectively.

22. The compound according to claim 1 wherein two amino acids at any of positions 2, 3, 4, 5, 8, 10, 11, 13, 16 and 18 have been replaced by an alternative amino acid.

23. The compound according to claim 1 wherein one amino acid at any of positions 2, 3, 4, 5, 8, 10, 11, 13, 16 and 18 has been replaced by an alternative amino acid.

* * * * *